(12) United States Patent
Taubman

(10) Patent No.: US 6,865,198 B2
(45) Date of Patent: Mar. 8, 2005

(54) CAVITY RINGDOWN SPECTROSCOPY SYSTEM AND METHOD

(75) Inventor: Matthew S. Taubman, Richland, WA (US)

(73) Assignee: Battelle Memorial Institute, Richland, WA (US)

(*) Notice: Subject to any disclaimer, the term of this patent is extended or adjusted under 35 U.S.C. 154(b) by 0 days.

(21) Appl. No.: 10/256,747

(22) Filed: Sep. 27, 2002

(65) Prior Publication Data
US 2004/0061859 A1 Apr. 1, 2004

(51) Int. Cl.[7] .................................................. H01S 3/13
(52) U.S. Cl. ................. 372/29.023; 372/18; 372/38.01; 372/29.011; 372/29.016; 372/29.02; 356/437
(58) Field of Search ............................ 356/437; 372/18, 372/38.01, 29.01, 29.011, 29.012, 29.013, 29.014, 29.015, 29.016, 29.02, 29.021, 29.022, 29.023, 30, 31, 32

(56) References Cited

U.S. PATENT DOCUMENTS

| | | | | |
|---|---|---|---|---|
| 3,575,669 | A | * | 4/1971 | Haeff ............................ 372/89 |
| 4,907,237 | A | * | 3/1990 | Dahmani et al. ............. 372/32 |
| 5,151,909 | A | * | 9/1992 | Davenport et al. ........... 372/22 |
| 5,528,040 | A | | 6/1996 | Lehmann |
| 5,717,708 | A | | 2/1998 | Mells |
| 5,903,358 | A | | 5/1999 | Zare et al. |
| 5,912,740 | A | | 6/1999 | Zare et al. |
| 5,973,782 | A | | 10/1999 | Bomse |
| 5,978,397 | A | | 11/1999 | Capasso et al. |
| 5,986,768 | A | | 11/1999 | Pipino |
| 6,005,878 | A | * | 12/1999 | Kung et al. ............... 372/29.01 |
| 6,084,682 | A | | 7/2000 | Zare et al. |
| 6,094,267 | A | | 7/2000 | Levenson et al. |
| 6,233,052 | B1 | | 5/2001 | Zare et al. |
| 6,373,570 | B1 | | 4/2002 | McFarland et al. |
| 6,377,350 | B1 | | 4/2002 | Paldus et al. |
| 6,396,856 | B1 | | 5/2002 | Sucha et al. |
| 6,400,744 | B1 | | 6/2002 | Capasso et al. |
| 6,466,322 | B1 | * | 10/2002 | Paldus et al. ................ 356/437 |
| 6,654,394 | B1 | * | 11/2003 | Sellin et al. .................... 372/32 |
| 2002/0101592 | A1 | | 8/2002 | Zare et al. |
| 2003/0058035 | A1 | * | 3/2003 | Taubman ..................... 327/560 |

FOREIGN PATENT DOCUMENTS

WO    WO 02/04903 A1    1/2002

OTHER PUBLICATIONS

Kosterev et al., Cavity Ringdown Spectroscopy of NO with a CW single frequency Quantum Cascade Laser, May 2001, Lasers and Electro–Optics, 2001. CLEO '01. Technical Digest, pp. 520–521.*

Jun Ye and John L. Hall, *Cavity ringdown heterodyne spectroscopy: High sensitivity with microwatt light power*, National Institute of Standards & Technology and University of Colorado, May 17, 2000.

* cited by examiner

*Primary Examiner*—Michael P. Stafira
*Assistant Examiner*—Juan D Valentin, II
(74) *Attorney, Agent, or Firm*—Woodard, Emhardt, Moriarty, McNett & Henry LLP

(57) ABSTRACT

One embodiment of the present invention includes an optical cavity, a source to provide light to the optical cavity, a sensor to detect the light and generate a corresponding sensor signal, and a servo device including a feedforward input and a feedback input. Feedback from the sensor signal is provided to the servo device to regulate operation of the source at a frequency selected to generate an optical field resonating in the first mode in the cavity. An input device provides a control signal to a control input of the servo device that selectively alters operation of the light source to corresponding halt resonance in the first mode. An evaluation device is also included to evaluate decay of the optical field after resonance in the first mode is halted.

15 Claims, 3 Drawing Sheets

US 6,865,198 B2

CAVITY RINGDOWN SPECTROSCOPY SYSTEM AND METHOD

GOVERNMENT RIGHTS

This invention was made with Government support under Contract Number DE-AC0676RLO1831. The Government has certain rights in the invention.

BACKGROUND

The present invention relates to cavity ringdown spectroscopy, and more particularly, but not exclusively relates to servo-switched frequency control of a light source for an optical resonator.

Cavity Ringdown Spectroscopy (CRDS) is a technique that, among other things, is directed to making absorption measurements with sensitivities that can be better than many other systems. In a typical CRDS system, the optical resonator includes two or more mirrors in an optical cavity aligned so that incident light circulates between them. The sample of absorbing material is placed in the cavity for interrogation. When input light to the resonator is discontinued, the radiant energy stored in the resonator decreases over time or "rings-down." For an empty cavity, the stored energy follows an exponential decay characterized by a ringdown rate that depends on the reflectivity of the mirrors, the separation between the mirrors, and the speed of light in the resonator. If an absorbing sample is placed in the resonator, the ringdown changes under appropriate conditions such that the resonator energy decays in a measurably different fashion than that for the empty resonator. A corresponding absorption spectrum for the sample is obtained by plotting the reciprocal of the ringdown rate versus the wavelength of the incident light. CRDS has been applied to numerous systems in the visible, ultraviolet, and infrared wavelength regimes. U.S. Pat. No. 5,528,040 to Lehmann is referred to as an additional source of background information concerning such techniques and is hereby incorporated by reference.

Current CRDS systems typically use a pulsed laser or a Continuous Wave (CW) laser. With a pulsed laser, the pulse length is generally much shorter than the ringdown time, so that less light enters the resonator compared to CW laser-based approaches. As a result, pulsed laser CRDS generally is less sensitive than CW laser CRDS. On the other hand, with CW laser CRDS, the need to switch the resonance off and on can be more complicated. Such switching is often performed with an Acousto-Optic Modulator (AOM), which can change the amplitude, frequency, and/or direction of the laser beam provided to the optical resonator, any one of which can be altered to initiate ringdown. Because an AOM provides a traveling wave with an acoustic grating that takes some time to form and dissipate, AOM switching typically has intrinsic speed limitations. These limitations can result in inaccuracies of the exponential fit of ringdown data, especially in the mid-wavelength to long-wavelength infrared ranges for which the AOM device is typically bigger and slower. For such wavelengths, the optical cavities of the corresponding resonators often have a lower resonance quality or "Q" factor, and correspondingly dissipate the decaying optical field faster during ringdown. In addition to drawbacks regarding the switching process, experiments of a more precise nature typically desire to "lock" the laser frequency to a selected resonant frequency, which is lost at the beginning of each ringdown interval and must be reacquired at the beginning of each excitation interval. These frequency lock techniques typically increase the complexity of the switching schemes used with CW laser CRDS.

Accordingly, there is a need for further contributions in this area of technology.

SUMMARY

One embodiment of the present invention is a unique technique for performing cavity ringdown spectroscopy. Other embodiments include unique systems, devices, apparatus, and methods for controlling operation of an optical resonator.

A further embodiment includes means for generating a resonating optical field including a light source coupled to an optical cavity; means for stabilizing the resonating optical field by providing feedback to the light source with servo circuitry coupled to the light source; and means for evaluating decay of the optical field in response to a control signal input to the servo circuitry. This control signal input can switch operation between two or more different resonant modes of the optical cavity by corresponding switching between different frequencies of a CW laser form of the light source.

Another embodiment of the present invention includes performing cavity ringdown spectroscopy with an optical resonator and a laser device. The laser device is stabilized with circuitry that receives a feedback signal corresponding to detected output light of the laser device. The circuitry further receives a control signal that can correspondingly cause a change in one or more output characteristics of the laser device, such that a selected resonant mode of the resonator can be readily discontinued to evaluate ringdown. In one form, switching between different resonant modes of the resonator is performed. The characteristics determined with this system can include evaluation of reflectivity of one or more mirrors included in the resonator and/or evaluation of a sample placed in the resonator. The circuitry can be in the form of a servo device with a feed forward input receiving the control signal and a feedback input receiving the detected heterodyne signal between the cavity mode and the incident field from the laser. The laser device can be in the form of a current-controlled continuous wave type, such as a quantum cascade laser or laser diode variety. The optical resonator can include two or more mirrors in an optical cavity. The optical cavity can be arranged to selectively receive an analyte for evaluation.

Another embodiment includes operating an optical cavity responsive to light and providing a feedback signal from a servo device to stabilize operation of the light source at a selected frequency. A control signal is also provided to the servo device to adjust operating frequency of the light source. The embodiment further includes switching between different resonant modes of the cavity in response to the control signal and evaluating decay for each of the different resonant modes.

Still another embodiment of the present invention includes providing light from a laser device to an optical resonator to operate the resonator in a first resonant mode; receiving a feedback signal representative of the light output with servo circuitry coupled to the laser device to stabilize operation of the resonator in the first resonant mode; and halting the operation of the cavity in the first resonant mode in response to a control signal provided to the circuitry to evaluate decay of an optical field corresponding to the first resonant mode. The laser device can be of a current-controlled continuous wave type such as a quantum cascade laser or laser diode variety and/or the servo circuitry can include a feed forward arrangement for receiving the control signal. The optical resonator can include two or more mirrors in an optical cavity arranged to selectively receive an analyte for evaluation.

Accordingly, one object of the present invention is to provide a unique technique for performing cavity ringdown spectroscopy.

Another object is to provide a unique system, method, device, or apparatus for controlling operation of an optical resonator.

Other objects, embodiments, forms, features, advantages, aspects and benefits of the present invention shall become apparent from the detailed description and drawings included herein.

DETAILED DESCRIPTION

Figure 1:
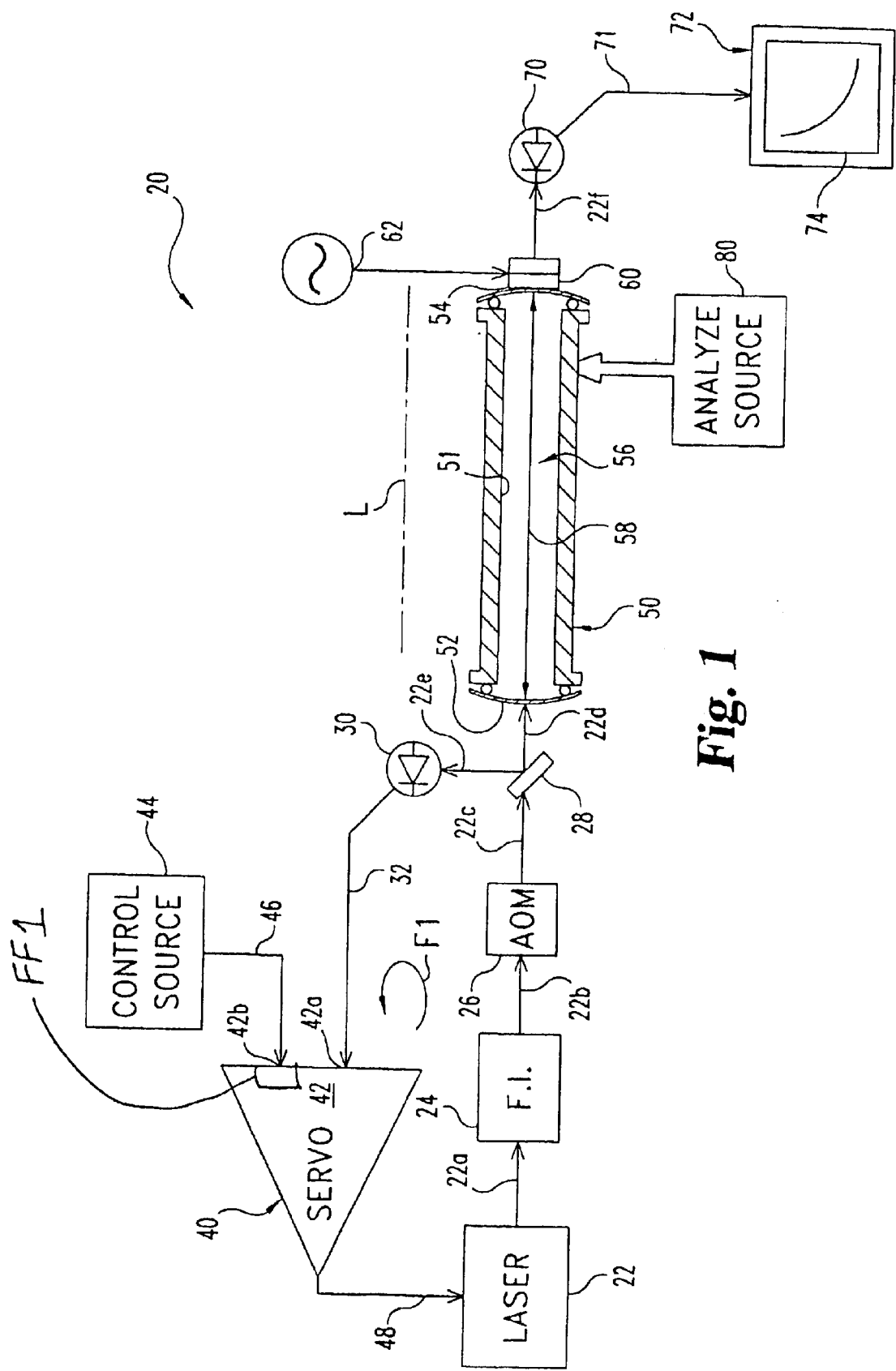
FIG. 1 is a diagrammatic view of an evaluation system of one embodiment of the present invention.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 diagrammatically depicts evaluation system 20 of one embodiment of the present invention. System 20 includes Continuous Wave (CW) laser 22 which generates a modulated light output along path 22a over an adjustable modulation frequency range. Laser 22 can be of any type generally capable of CW operation, and may be tunable over a desired range of wavelengths. In one form, laser 22 is of a current-controlled, laser diode or quantum cascade laser variety, to name just a few examples. Laser 22 provides light in the form of a generally coherent beam which is provided along path 22a to a standard Faraday Isolator (FI) 24. From isolator 24, light continues along path 22b to Acousto-Optic Modulator (AOM) 26 which provides further isolation as will be explained hereinafter. From AOM 26, the light continues on path 22c to beam splitter 28 which allows some or all of the incident beam from path 22c to pass through, following path 22d. Light along path 22d enters optical resonator 50 of system 20. A heterodyne signal is formed by combining some of the reflected input from path 22d and backwardly propagated light from resonator 50, which is deflected by beam splitter 28, allowing this combined optical field to be incident on the detector 30 along path 22e. Frequently, beam splitter 28 returns some portion of light toward AOM 26 along path 22c. AOM 26 is effective to reduce, if not completely block, the return of such light to laser 22 from beam splitter 28. Beam splitter 28 symbolically represents any of a number of different arrangements, including, but not limited to, a simple nonpolarizing beam splitter, a polarizing beam splitter, or a combination of a quarter-wave plate or rhomb and a polarizing or (nonpolarizing) beam splitter.

Resonator 50 includes enclosure 51 and mirrors 52 and 54 disposed therein. Mirrors 52 and 54 are oppositely positioned and separated from one another along longitudinal axis L of resonator 50. Mirrors 52 and 54 are each of a concave, spherically-shaped type disposed in optical cavity 56 defined by enclosure 51. Typically, light from path 22d enters cavity 56 at an angle such that it impinges on one of mirrors 52 and 54, which is aligned to reflect the incident light toward the other of mirrors 52 and 54 along separation distance 58, which is symbolically represented by a double-headed arrow. Accordingly, an optical field can be generated along the optical path of separation distance 58 between mirrors 52 and 54. Optical cavity 56 has transmission and reflection resonances at periodic frequencies for which the resulting optical field has a greater intensity than that provided by the incident light from laser 22. By tuning the input light from laser 22 to one or more of these frequencies, a resonance mode of the optical field can be stimulated.

System 20 further includes adjustment device 60. The length of separation distance 58 can be varied or "tuned" with device 60, which includes one or more elements to selectively translate mirror 54 along longitudinal axis L relative to mirror 52. Device 60 is responsive to a periodic input signal from signal source 62 to correspondingly adjust separation distance 58 at periodic rate. The change in distance 58 can likewise change resonance properties of cavity 56 providing a sweep for resonance over a selected range. In one form, device 60 is of an electromechanical variety that could include one or more piezoelectric actuators, and the signal from source 62 is of a sawtooth or triangle waveform type to provide the corresponding sweep. In other embodiments, a different aperiodic or periodic signal may be used, or device 60 and/or source 62 may be absent. Alternatively or additionally, in other embodiments variation in optical cavity resonances can be obtained by making adjustments to laser 22, and/or through different changes to resonator 50.

An output light beam from resonator 50 is provided along path 22f to sensor 70 of system 20. Sensor 70 generates a signal corresponding to the intensity of the output light from resonator 50, which is provided along pathway 71 to evaluation device 72 of system 20. For a given resonance mode of optical cavity 56, the corresponding optical field takes a length of time to build-up and decay. The ringdown (decay) time is a function of the quality or "Q" of optical cavity 56. If optical cavity 56 contains a small quantity of a gaseous analyte that absorbs light at the operating wavelength, the Q of cavity 56 can be degraded, thus changing the peak cavity field and the ringdown (decay) time. Comparative measurements of this ringdown time with and without the analyte can result in a sensitive measurement of the optical field absorption by the analyte introduced into the cavity, which can be desirable for detecting concentration of one or more chemicals comprising the analyte. Alternatively or additionally, cavity ringdown can be used to measure very small looses or changes in the properties of reflective coatings of mirror 52 and/or mirror 54.

In further embodiments of system 20, sensor 30 can in addition to the laser control functions already outlined above, in fact be used to perform the above-described ringdown detection function of sensor 70. For this alternate embodiment, (sometimes called CW Heterodyne Ring Down), during the ringdown time of the optical cavity, the frequency of the incident laser light in path 22d which is in addition reflected from the front mirror 52 of optical cavity 56, is detuned from the light emanating from a decaying mode of the same. Light from the decaying mode propagates backward along path 22d and is coincident with the direct reflection of the detuned incident field. This collinear field pair produces a heterodyne beat signal on sensor 30 in simultaneous addition to, but not in conflict with, other signals which can be produced to effect the locking of the laser 22 to another arbitrary mode of optical cavity 56. This heterodyne beat signal exhibits the same ringdown character as those generated by sensor 70, but in fact with more sensitivity.

Device 72 is depicted as a device which includes display 74 that schematically portrays the exponential decay of an optical field in cavity 56 that might result from discontinuing input light tuned to a desired resonant mode. It may also in fact be a computer which measures the ringdown time by performing real-time curve-fitting analysis to find the ringdown time constants, allowing this constant to be plotted in time as the cavity is scanned, showing the absorption features of the analyte by fluctuations in the ringdown time. Analyte source 80 selectively provides a substance (analyte) through an opening in enclosure 51 to cavity 56 for evaluation. Typically this analyte is in a gaseous form. The decay characteristics for one or more resonant modes of cavity 56 are determined and compared to "empty cavity" decay patterns. This comparison yields information useful in quantifying the analyte of interest.

Returning to beam splitter 28 of system 20, the light beam along path 22e is monitored with optical sensor 30. Sensor 30 generates a signal along pathway 32 that is responsive to the intensity of the light it detects. Sensors 30 and 70 can be of the same or different types, including, but are not limited to, a photodiode, a photomultiplier tube, or a different variety as would occur to one skilled in the art.

System 20 also includes laser stabilization circuitry 40 in the form of servo 42. Servo 42 is further schematically depicted with feedback input 42a and control input 42b. Feedback input 42a receives the sensor signal from pathway 32. Control input 42b receives a control signal from control signal source 44 via pathway 46. Servo 42 outputs a laser control signal along pathway 48 to direct and regulate operation of laser 22.

It should be appreciated that two or more of laser 22, FI 24, AOM 26, beam splitter 28, sensor 30, sensor 70, resonator 50, device 60, source 62, device 72, source 44, and circuitry 40 can integrated together into a common unit along with any operatively connecting paths or pathways. Laser 22, device 72, source 62, source 44, sensor 30, sensor 70, or circuitry 40 can include one or more connections in common with one or more computing and/or control systems, power supplies, or the like. Although not shown, it should be appreciated that equipment to regulate one or more environmental characteristics of any or all the optical and/or electrical components of system 20 can be utilized; where such characteristics include, but are not limited to temperature, humidity, and pressure. Light paths 22a–22f can be through atmosphere, free space, one or more optical fibers, optical couplers, a combination of these, and/or such different arrangements as would occur to one skilled in the art to facilitate the desired light transmission. Pathways 32, 46, 48, and 71 are typically of an electrical conducting type to transmit corresponding electronic signals of a varying voltage and/or current variety.

During operation of system 20, stabilization circuitry 40 is responsive to feedback from sensor 30 to lock operation of laser 22 at a modulation frequency via pathway 48 selected to excite a desired resonance mode in optical cavity 56. This feedback path is symbolized by feedback loop F1 in FIG. 1. In one embodiment, feedback loop F1 is implemented by determining a frequency difference or "error" between the laser output light detected with sensor 30 and the desired frequency. For such an arrangement, circuitry 40 could be arranged to determine frequency from the signal at input 42a and compare it to a target frequency, then generate a corrective output to laser 22 via pathway 48. Such an arrangement could be based on one or more differential amplifiers of an operational amplifier (opamp) variety or different type. In one opamp-based form, a negative opamp input could receive a voltage corresponding to the measured modulation frequency of light detected with sensor 30 and a positive input could receive a voltage level corresponding to a target modulation frequency (not shown).

Circuitry 40 is further arranged to receive a modulation frequency control signal from source 44 via pathway 46 at input 42b. Circuitry 40 is arranged to respond to certain levels of the control signal to change the frequency of operation of laser 22. As a result, an optical field resonance in cavity 56 corresponding to a given frequency can be halted, permitting a ringdown of this resonance. In one embodiment, it has been found that frequency control in this manner can be implemented using feed forward circuitry FF1 associated with servo 42. Alternatively, circuitry 40 can respond to a change in the frequency control signal from source 44 such that it alters the modulation frequency of light output by laser 22 to provide a different mode of resonance in cavity 56. In this way, laser 22 and circuitry 40 can be arranged to switch operation of resonator 50 between two or more different cavity resonance modes to correspondingly provide different ringdown (decay) measurements. Accordingly, an alternating (AC) ringdown technique can be performed which switches between two cavity modes, one of which is within and the other of which is outside the absorption band of the analyte. This approach allows the baseline comparison and the analyte data to be measured in rapid succession, which typically increases the signal-to-noise ratio of the system. Alternatively or additionally, the switching of modulation frequencies with circuitry 40 optionally eliminates the need for switching with an AOM type device 26. Indeed, while AOM 26 could alternatively or additionally be used in such mode, it can be retained for isolation purposes only as illustrated and described in connection with FIG. 1. In one form, the control signal 44 is of a periodic square waveform type that correspondingly switches operation of resonator 50 between two cavity modes via circuitry 40 and laser 22.

Figure 2:
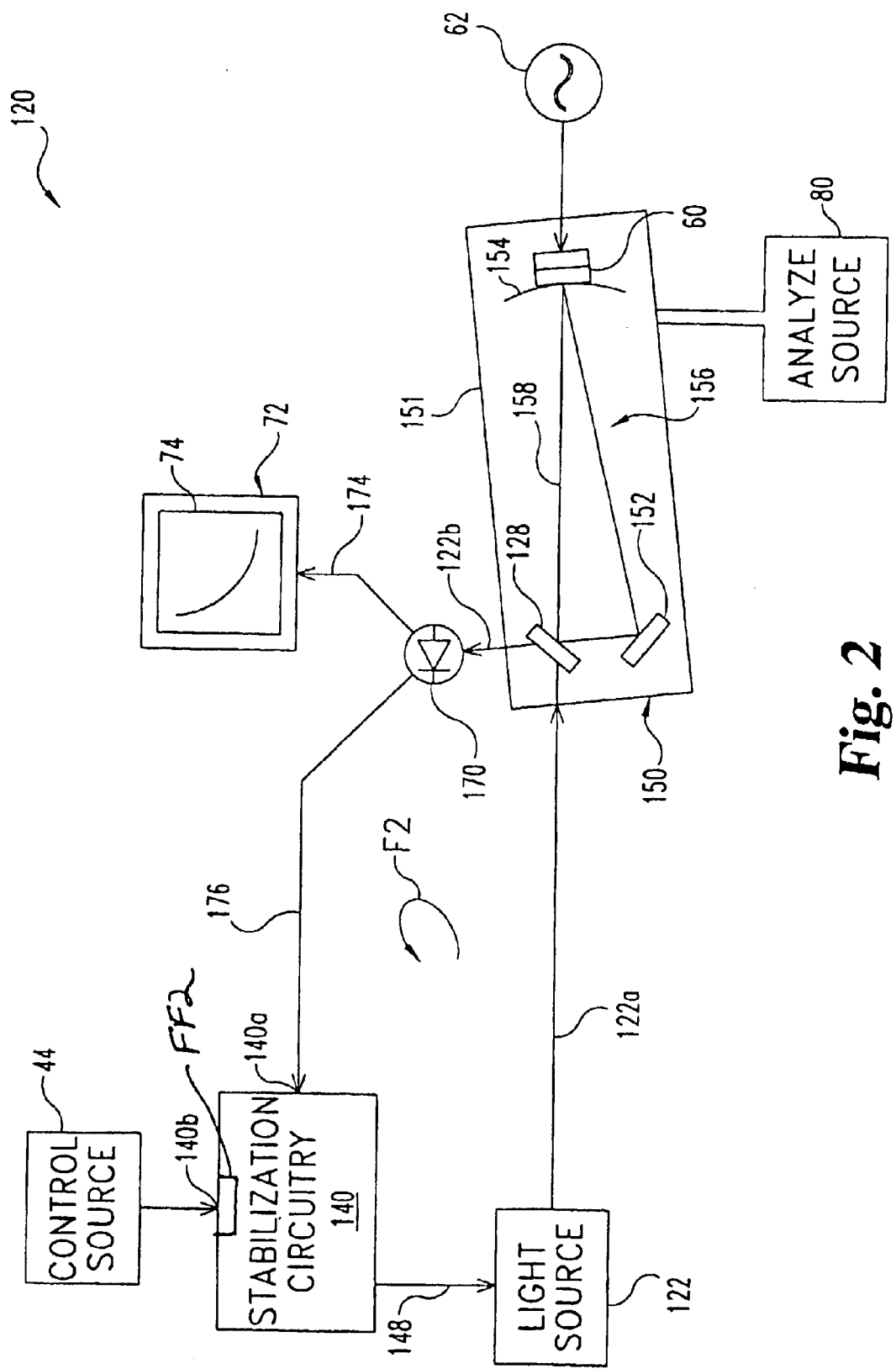
FIG. 2 is a diagrammatic view of an evaluation system of another embodiment of the present invention.

Referring to the schematic representation of FIG. 2, system 120 of another embodiment of the present invention is depicted; where like reference numerals refer to like features. System 120 includes light source 122 providing a light beam along path 122a of a selected character. In one form, source 122 provides light over a selected range of modulation frequencies and optionally, can be tunable over a range of wavelengths. Source 122 can include a laser device or other source appropriate to provide modulated light of a desired wavelength and frequency.

The light along path 122a is provided to excite optical resonator 150 of system 120. Resonator 150 includes enclosure 151, beam coupling mirror 128, mirror 152, mirror 154, and adjustment device 60. Enclosure 151 defines optical cavity 156 in which coupling mirror 128, mirror 152, and mirror 154 are disposed. Incident light from path 122a is split into two different beams by coupling mirror 128. One of these beams is directed into the optical cavity ring comprising coupling mirror 128 itself, mirror 154 and mirror 152 to define an optical mode within the ring. The other beam is deflected directly on to sensor 170, which is comprised of combined light emanating from the cavity mode 158 to produce a heterodyne signal to provide signals desired for control of the laser via pathways 176 and 148, and the ringdown signal via pathway 174. This arrangement facilitates development of a circulating optical field designated by reference numeral 158 in FIG. 2.

Mirror 152 and coupling mirror 128 each have a generally planar reflecting surface, while mirror 154 is of a concave, spherical type aligned relative to mirror 152 and coupling mirror 128 to provide the optical ring path. Mirror 154 is engaged by adjustment device 60 which is coupled to signal source 62. Device 60 and source 62 can operate as described in connection with like reference numerals of FIG. 1 to adjust separation distances between mirror 154 and coupling mirror 128 and/or mirror 152. Resonator 150 operates in a manner analogous to resonator 50 in that frequency-dependent resonance can be sustained at an energy level greater than the input light from source 122. Further, multiple resonance modes can be selectively stimulated. A part of the light from field 158 exits through coupling mirror 128 along path 122b. Optical paths 122a and 122b can be through atmosphere, free space, one or more optical conductors, optical couplers, any combination of these, or such different arrangement as would occur to those skilled in the art.

Sensor 170 of system 120 detects intensity of light from resonator 150 via path 122b to provide a corresponding sensor signal. Sensor 170 can be of any type, such as those described in connection with sensors 30 and 70 of system 20. The signal from sensor 170 is provided along pathway 174 to evaluation device 72 of system 120. Evaluation device 72 includes display 74 as were previously described in connection with system 20. The sensor signal is also provided along pathway 176 to stabilization circuitry 140 of system 120. Stabilization circuitry 140 receives the sensor signal through input 140a which is used as feedback to adjust the output of source 122 via pathway 148. Accordingly, stabilization circuitry 140 can define or include a servo device or circuit suitable to operate a laser form of source 122 via pathway 148 as described in connection with laser 22 and circuitry 40 of system 20.

Stabilization circuitry 140 operates to lock the modulation frequency of output light from source 122 at a value desired to establish/sustain a resonating optical field 158. This feedback loop is schematically designated by reference numeral F2 in FIG. 2. Control source 44 provides a frequency control signal to circuitry 140 via input 140b. Circuitry 140 is responsive to change modulation frequency of light output by source 122 via a source control signal along pathway 148, such that a given resonance of resonator 150 is halted. Alternatively or additionally, stabilization circuitry 140 can be arranged to respond to the control signal from source 44 to switch between one or more different resonant modes of resonator 150. In one form including a servo device, the frequency control signal from source 44 can be provided to a feed forward type of arrangement FF2 associated with the servo.

When a resonance mode is discontinued or switched, the sensor signal to device 72 via pathway 174 can be utilized to comparatively evaluate decay or ringdown in the manner previously described. It should be appreciated that system 120 does not include a Faraday isolator or AOM, although such additional devices might be utilized in other embodiments. Nevertheless, in many embodiments it is frequently desirable to exclude isolators, AOMs, and the like, which is made possible by the present invention. By using a ring cavity such as that defined by resonator 150, reduces the returned signal along pathway 122a can be reduced to backscatter and reflection from sensor 170 back through the ring, which are often manageable in desired implementations. Allowing removal of Faraday isolators and AOMs, which in Long Wavelength InfraRed (LWIR) are typically bulky and inefficient, can be particularly desirable. System 120 further includes analyte source 80 which can be used to selectively introduce an analyte into optical cavity 156 for analysis in the manner previously described.

It should be appreciated that two or more of source 122, resonator 150, device 60, source 62, sensor 170, device 72, source 44, and circuitry 140 can integrated together into a common unit along with any operatively connecting paths or pathways. Source 122, device 72, source 62, source 44, sensor 170, or circuitry 140 can include one or more connections in common with one or more computing and/or control systems, power supplies, or the like. Although not shown, it should be appreciated that equipment to regulate one or more environmental characteristics of any or all the optical and/or electrical components of system 120 can be utilized; where such characteristics include, but are not limited to temperature, humidity, and pressure. Pathways 174 and 176 are typically of an electrical conducting type to transmit corresponding electronic signals of a varying voltage and/or current variety.

EXPERIMENTAL EXAMPLE

The present invention will be further described with reference to the following specific example. It will nevertheless be understood that this example is merely illustrative and is not intended to restrict or otherwise limit the scope of the present invention.

Figure 3:
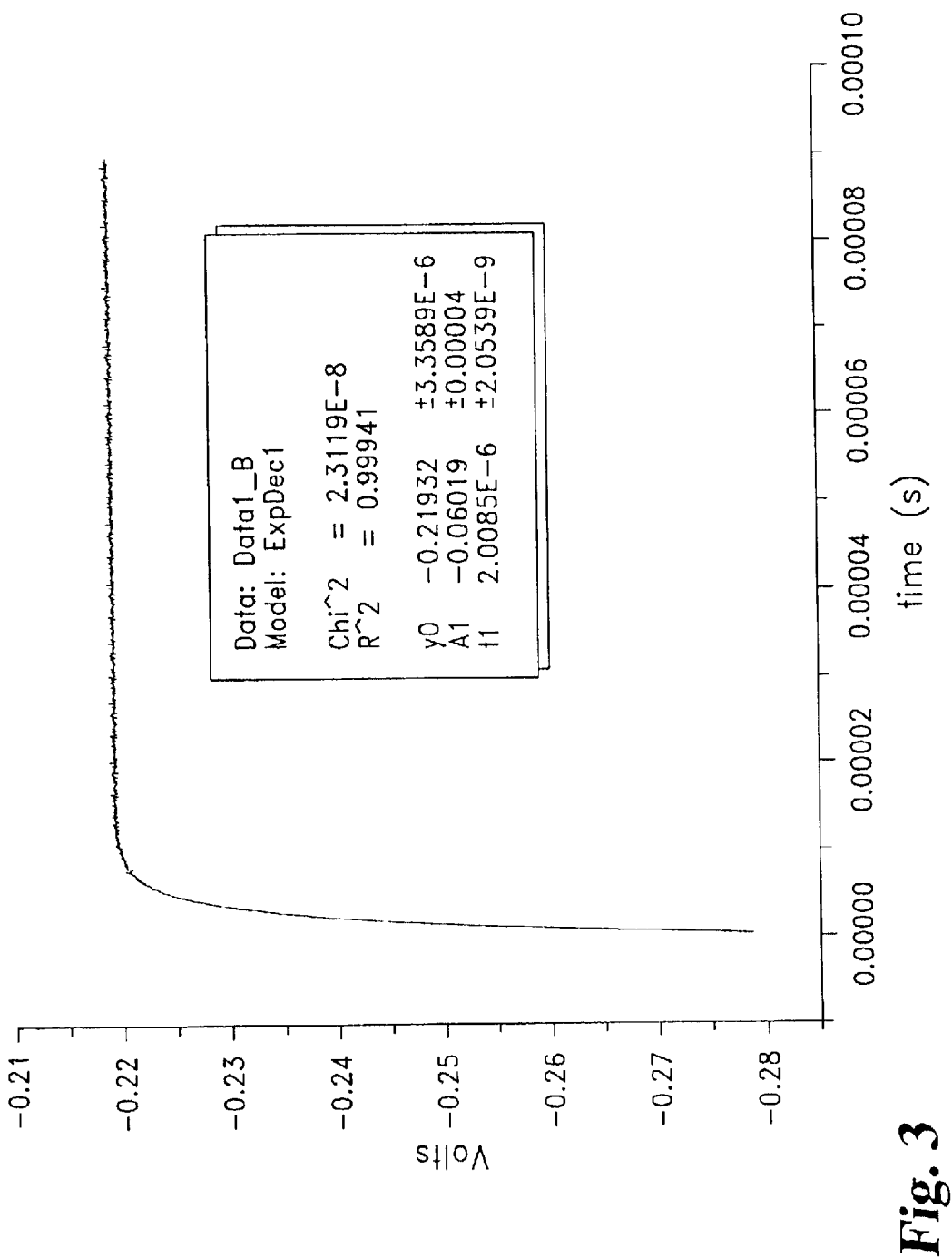
FIG. 3 is a graph of experimental results obtained with a system according to the present invention.

FIG. 3 shows ringdown data taken with an experimental arrangement of the type shown in FIG. 1. This arrangement shows an inverted exponential decay averaged over 100 sweeps, and a weighted exponential fit. It should be understood that the relatively quick and reproducible switching available with this technique allows meaningful averages to be taken without drift, washout, or various noise effects. The parameters of the exponential fit determine the ringdown time, facilitating a quick and accurate determination of the reflectivities of the mirrors used in the optical cavity. Similar experiments can be conducted to evaluate analytes as previously described in connection with FIGS. 1 and 2.

Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method, comprising:

providing a light output from a laser device to an optical cavity to operate the cavity in a first resonant mode;

receiving a feedback signal representative of the light output with servo circuitry coupled to the laser device to stabilize operation of the cavity in the first resonant mode; and halting the operation of the cavity in the first resonant mode in response to a control signal provided to the circuitry to evaluate decay of an optical field corresponding to the first resonant mode, said halting including performing feedforward control with the circuitry.

2. The method of claim 1, which includes sensing the light output with an optical sensor to generate the feedback signal.

3. The method of claim 1, wherein said halting includes changing operation of the cavity from the first resonant mode to a second resonant mode in response to the control signal.

4. The method of claim 1, wherein the laser device includes a quantum cascade laser responsive to current flow provided by the circuitry.

5. The method of claim 1, which includes sensing the light output with an optical sensor to generate the feedback signal and a signal corresponding to the decay of the optical field.

6. The method of claim 1, which includes providing an acousto-optic modulator in an optical pathway between the laser device and the cavity.

7. The method of claim 1, which includes:
providing the feedback signal from a photodetector coupled to a first input of the servo circuitry; and
providing a feedforward control signal from a control source coupled to a second input of the servo circuitry.

8. The method of claim 1, wherein the laser device includes a laser, and further comprising:
changing operation of the laser in response to the control signal; and
alternating operation of the cavity between the first resonant mode and a second resonant mode.

9. A method, comprising:
operating an optical cavity responsive to light from a light source;
providing a feedback signal to a servo device to stabilize operation of the source at a selected frequency and a control signal to the servo device to adjust operating frequency of the light source, said providing including performing feedforward control with the servo device;
switching between different resonant modes of the cavity in response to the control signal; and
evaluating decay for each of the different resonant modes.

10. The method of claim 9, which includes providing an analyte to the cavity for said evaluating.

11. The method of claim 9, which includes sensing the light to generate the feedback signal and an evaluation signal for said evaluating.

12. The method of claim 9, wherein the source includes a quantum cascade laser.

13. The method of claim 12, wherein said providing includes regulating the quantum cascade laser in response to electrical current provided by the servo device.

14. The method of claim 9, wherein the feedback signal is provided from a photodetector coupled to a first input of the servo device and the control signal is provided from a control source coupled to a second input of the servo device.

15. The method of claim 9, wherein said switching includes alternating operation of the cavity between the different resonant modes.

* * * * *